(12) United States Patent
Wang et al.

(10) Patent No.: US 12,168,096 B2
(45) Date of Patent: Dec. 17, 2024

(54) VENTILATOR-WEANING TIMING PREDICTION SYSTEM, PROGRAM PRODUCT THEREOF AND METHOD FOR BUILDING AND USING THE SAME

(71) Applicant: CHIMEI MEDICAL CENTER, Tainan (TW)

(72) Inventors: Jhi-Joung Wang, Tainan (TW); Hung-Jung Lin, Tainan (TW); Kuo-Chen Cheng, Tainan (TW); Shian-Chin Ko, Tainan (TW); Chin-Ming Chen, Tainan (TW); Shu-Chen Hsing, Tainan (TW); Mei-Yi Sung, Tainan (TW); Chung-Feng Liu, Tainan (TW); Chia-Jung Chen, Tainan (TW)

(73) Assignee: ChiMei Medical Center, Tainan (TW)

( * ) Notice: Subject to any disclaimer, the term of this patent is extended or adjusted under 35 U.S.C. 154(b) by 863 days.

(21) Appl. No.: 17/159,342

(22) Filed: Jan. 27, 2021

(65) Prior Publication Data
US 2022/0233799 A1   Jul. 28, 2022

(51) Int. Cl.
*A61M 16/00* (2006.01)
*A61B 5/00* (2006.01)
(Continued)

(52) U.S. Cl.
CPC ....... *A61M 16/026* (2017.08); *A61B 5/02055* (2013.01); *A61B 5/14542* (2013.01);
(Continued)

(58) Field of Classification Search
CPC ...... A61M 16/024; A61B 5/00; A61B 5/0205; A61B 5/02055; A61B 5/02141; A61B 5/024; A61B 5/08; A61B 5/0813; A61B 5/082; A61B 5/083; A61B 5/0833; A61B 5/085; A61B 5/087; A61B 5/0871; A61B 5/091; A61B 5/0935; A61B 5/097; A61B 5/4833; A61B 5/4836; A61B 5/7264; A61B 5/7271; A61B 5/7275; A61B 5/74; A61B 5/742; A61B 5/743; A61B 5/7435; G06N 5/025; G06N 7/00; G06N 7/023; G06N 7/06; G06N 7/08; G06N 20/00; G06N 20/10; G06N 20/20; G16H 10/60; G16H 20/30; G16H 20/40; G16H 40/00;
(Continued)

(56) References Cited

U.S. PATENT DOCUMENTS 7,845,350 B1* 12/2010 Kayyali ............ A61M 16/0051
128/204.23
2006/0271407 A1* 11/2006 Rosenfeld .............. G16H 50/20
434/262
(Continued)

FOREIGN PATENT DOCUMENTS

CN    110179465 A    8/2019
TW    201023831 A    7/2010

*Primary Examiner* — Joseph D. Boecker
*Assistant Examiner* — Jaeick Jang
(74) *Attorney, Agent, or Firm* — Rosenberg, Klein & Lee

(57) ABSTRACT

A ventilator-weaning timing prediction system, a program product therefor, and methods for building and using the same are disclosed to help a physician to determine a timing for a ventilator-using patient to try to weaning or completely wean from mechanical ventilation using AI-based prediction.

8 Claims, 11 Drawing Sheets

(51) Int. Cl.

| | |
|---|---|
| *A61B 5/0205* | (2006.01) |
| *A61B 5/021* | (2006.01) |
| *A61B 5/145* | (2006.01) |
| *G06N 5/04* | (2023.01) |
| *G06N 20/00* | (2019.01) |
| *G16H 10/60* | (2018.01) |
| *G16H 20/40* | (2018.01) |
| *G16H 40/40* | (2018.01) |
| *G16H 40/67* | (2018.01) |
| *G16H 50/20* | (2018.01) |
| *G16H 50/30* | (2018.01) |
| *A61B 5/024* | (2006.01) |
| *A61B 5/08* | (2006.01) |
| *A61B 5/091* | (2006.01) |

(52) U.S. Cl.
CPC ......... *A61B 5/7203* (2013.01); *A61B 5/7267* (2013.01); *A61B 5/7275* (2013.01); *G06N 5/04* (2013.01); *G06N 20/00* (2019.01); *G16H 10/60* (2018.01); *G16H 20/40* (2018.01); *G16H 40/40* (2018.01); *G16H 40/67* (2018.01); *G16H 50/20* (2018.01); *G16H 50/30* (2018.01); *A61B 5/021* (2013.01); *A61B 5/024* (2013.01); *A61B 5/0816* (2013.01); *A61B 5/091* (2013.01)

(58) Field of Classification Search
CPC ........ G16H 40/20; G16H 40/40; G16H 40/60; G16H 40/63; G16H 40/67; G16H 50/20; G16H 50/30
See application file for complete search history.

(56) References Cited

U.S. PATENT DOCUMENTS

| | | | |
|---|---|---|---|
| 2018/0185642 A1* | 7/2018 | Lu | A61N 2/02 |
| 2022/0241530 A1* | 8/2022 | Hanafialamdari | A61B 5/087 |
| 2023/0211100 A1* | 7/2023 | Villasmil | G16H 20/40 |
| | | | 128/204.23 |

* cited by examiner

FIG. 5

| Nursing station | Bed No | Medical record No. | Name | Start time | Hours so far | 8hr | 12hr | 24hr | 36hr | 48hr | 60hr | 72hr | 84hr | 96hr | 108hr | 120hr |
|---|---|---|---|---|---|---|---|---|---|---|---|---|---|---|---|---|
| 3BI | 3BI20 | | | 2020-10-12 22:00 | 59 | 59.93% | 28.8% | 58.2% | 72.53% | 76.6% | 79.67% | 82.8% | 84.9% | 87% | 89.5% | 92.3% |
| | | | | | | | | | | | | | | | | |
| | | | | | | | | | | | | | | | | |
| | | | | | | | | | | | | | | | | |
| | | | | | | | | | | | | | | | | |

Ventilator-weaning timing prediction (Try-Weaning)

12

F I G . 6

| Nursing station | Bed No | Medical record No. | Name | Start time | Hours so far | 24hr | 48hr | 72hr | 96hr | 120hr | 144hr | 168hr | 192hr | 216hr | 240hr | 264hr |
|---|---|---|---|---|---|---|---|---|---|---|---|---|---|---|---|---|
| 3BI | 3BI20 | | | 2020-10-12 22:00 | 59 | 42.3% | 48.7% | 52.6% | 65.3% | 70.1% | 73.3% | 78.2% | 83% | 86.5% | 89.3% | 93.2% |
| | | | | | | | | | | | | | | | | |
| | | | | | | | | | | | | | | | | |
| | | | | | | | | | | | | | | | | |
| | | | | | | | | | | | | | | | | |

Ventilator-weaning timing prediction (Complete-Weaning)

12

F I G . 7

Ventilator-weaning prediction (Complete-Weaning)

| Medical record No. | xxxxxxxx | Name | x x x |

Ventilator-weaning

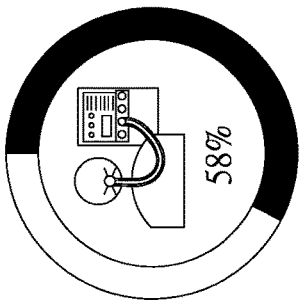

58%

| Feature variables | Raw prediction | Adjusted prediction |
|---|---|---|
| Age | 44 | 44 |
| APACHE II score | 8 | 8 |
| TISS score | 36 | 36 |
| Coma score-eye opening | 6 | 6 |
| Coma score-motor response | 6 | 6 |
| Inspired oxygen fraction | 40 | 40 |
| Positive end-expiratory pressure | 8 | 8 |
| Respiratory rate | 14 | 40 |
| Minute ventilation | 11.6 | 11.6 |
| Peak inspiratory pressure | 26 | 26 |
| Mean airway pressure | 12 | 12 |
| Support pressure | 3 | 3 |
| Expiratory tidal volume | 828 | 828 |
| Cuff leak test | 30 | 30 |
| Maximum expiratory pressure | 80 | 80 |
| SBT count | 2 | 2 |
| Heart rate | 78 | 78 |
| Systolic blood pressure | 123 | 123 |
| Diastolic blood pressure | 84 | 84 |
| Blood oxygen saturation | 100 | 100 |
| Body temperature | 36.5 | 36.5 |
| Count of sputum suction | 7 | 7 |

F I G. 9

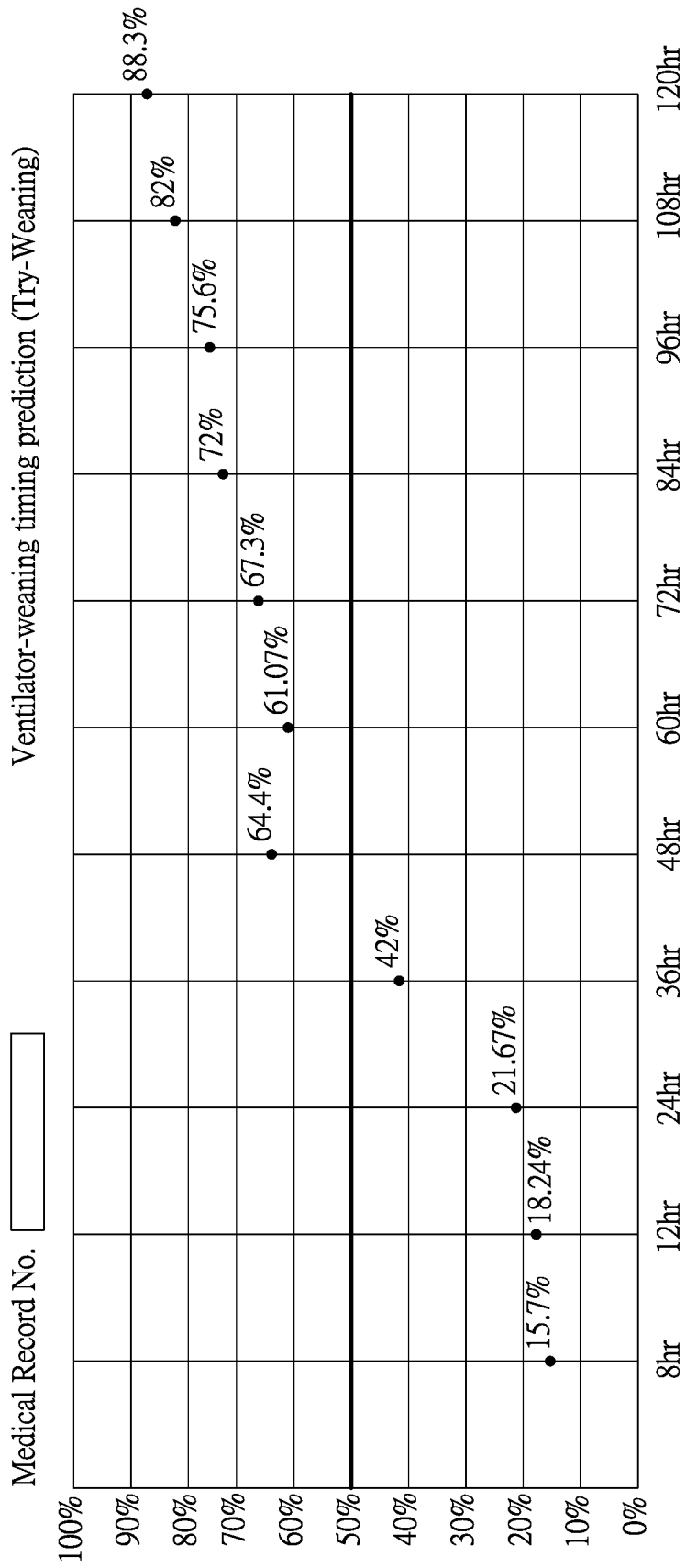
F I G . 10

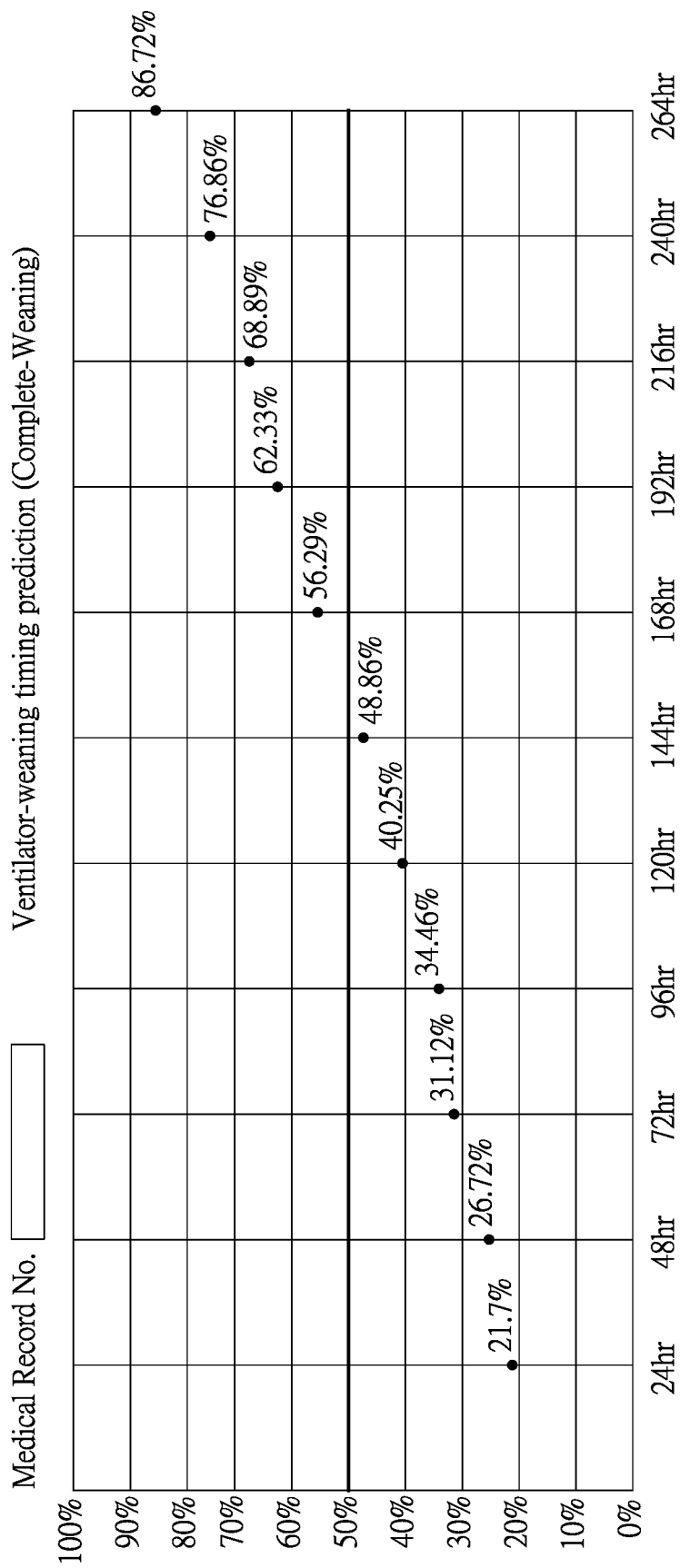
F I G . 11

VENTILATOR-WEANING TIMING PREDICTION SYSTEM, PROGRAM PRODUCT THEREOF AND METHOD FOR BUILDING AND USING THE SAME

BACKGROUND OF THE INVENTION

1. Technical Field

The present invention relates to a ventilator-weaning timing prediction system, a program product therefor and methods for building and using the same. The present invention aims to help a physician to determine a timing for a ventilator-using patient to try to weaning or completely wean from mechanical ventilation using AI-based prediction.

2. Description of Related Art

As to caring critically ill patients, it is important to minimize the duration of use of respiratory assistance in order to prevent potential complications and save medical costs. However, premature or late weaning may cause adverse reactions. This makes it clinically essential to properly determine the timing for a patient to stop using mechanical ventilation.

During practical respiratory treatment, the timing is determined based on the results of try-weaning. The practice of "try-weaning" involves switching the ventilator from the control mode to the support mode before complete-weaning (or using oxygen only) can be carried out. Properly timed try-weaning and complete-weaning can be helpful to reduce the probability of re-intubation and effectively minimize the time of ventilator using. Currently, there is no reliable data sources to support timing decisions for successful try-weaning and complete weaning, and medical staff usually make such decisions according to their clinical experience and medical norms. While the conventional practice is proven by a relatively high success rate, the conservative estimation is not helpful for minimizing the duration of ventilator usage. However, in fact, as cited in many literatures, there are 70% of total patients could have earlier try-weaning then they actually received, and there are about 50% to the total patient could be extubated earlier without re-intubation.

SUMMARY OF THE INVENTION

Therefore, the present inventors use AI-based machine learning technology to build a try-weaning timing model and further develop the model into an information system for suggesting the best "try-weaning timing" and "complete-weaning timing" to medical staff, on the basis of medical big data about ventilator using in the Chi Mei Medical Center (Taiwan), expert experience as well as the internationally recognized ventilator-weaning literature such as the WEANSNOW Score (Wake, Electrolytes, Acidosis/Alkalosis, Neuromuscular, Suctioning/Secretions, Nutritionally intact, Obstruction, Weaning parameters).

Hence, the present invention provides a method for building a ventilator-weaning timing prediction system, configured to predict a timing for a ventilator-using patient to receive ventilator-weaning, the method comprising:

a step of acquiring weaning-related medical data: capturing the weaning-related medical data among original data stored in a medical database.

a step of performing model training based on AI learning: cleaning and transforming the weaning-related medical data to obtain a plurality of feature variables to be entered into a big data database, and using at least one algorithm to perform a model training based on AI learning according to the feature variables, in which the feature variables include the patient's age, disease severity, patient ventilator parameters and physiological sign parameters.

a step of acquiring a prediction model: obtaining at least one prediction model as a result of the model training of the previous step, in which the prediction model includes a plurality of ventilator-weaning timeframes and corresponding predicted success probabilities for weaning.

a step of building web-based services: providing a medical information system service interface program, a feature value capturing service program and a weaning prediction service program; the medical information system service interface program being connected to a medical information system, so as to enable the medical information system to call for the medical information system service interface program, and to enable the feature value capturing service program to capture a medical feature value of the ventilator-using patient from the medical database, so that the weaning prediction service program conducts prediction using the at least one prediction model according to the medical feature value, and returns a prediction result to the medical information system service interface program.

Further, the timing to receive ventilator-weaning refers to a timing for the ventilator-using patient to perform try-weaning. Among the feature variables, the disease severity includes a score obtained using the Acute Physiology and Chronic Health Evaluation II, and a score measured using a Therapeutic Intervention Scoring System. The ventilator parameters include the patient's inspired oxygen fraction, positive end-expiratory pressure, respiratory rate, minute ventilation, peak inspiratory pressure, mean airway pressure, support pressure, and expiratory tidal volume. The physiological sign parameters include the patient's heart rate, systolic blood pressure, diastolic blood pressure, and blood oxygen level. The at least one prediction model is a first prediction model. The first prediction model includes try-weaning in 8 hours, try-weaning in 12 hours, try-weaning in 24 hours, try-weaning in 36 hours, try-weaning in 48 hours, try-weaning in 60 hours, try-weaning in 72 hours, try-weaning in 84 hours, try-weaning in 96 hours, try-weaning in 108 hours, and try-weaning in 120 hours. Thereby the weaning prediction service program conducts prediction using the first prediction model according to the medical feature value, and returns the first prediction result to the medical information system service interface program.

Further, the timing to receive ventilator-weaning refers to a timing for the ventilator-using patient to completely wean from mechanical ventilation. Among the feature variables, the disease severity includes a score obtained using the Acute Physiology and Chronic Health Evaluation II, a score measured using a Therapeutic Intervention Scoring System, coma score-eye opening, and coma score-motor response. The ventilator parameters include the patient's inspired oxygen fraction, positive end-expiratory pressure, respiratory rate, minute ventilation, peak inspiratory pressure, mean airway pressure, support pressure, expiratory tidal volume, cuff leak test, maximum expiratory pressure, and a count of spontaneous breathing trials (SBT). The physiological sign parameters include the patient's heart rate, systolic blood pressure, diastolic blood pressure, blood oxygen level, body temperature, and a count of sputum suction. The at least one prediction model is a second prediction model. The second prediction model includes weaning in 24 hours, weaning in 48 hours, weaning in 72 hours, weaning in 96 hours, weaning in 120 hours, weaning in 144 hours, weaning in 168 hours, weaning in 192 hours, weaning in 216 hours, weaning in 240 hours, and weaning in 264 hours. Thereby, the weaning prediction service program conducts prediction using the second prediction model according to the medical feature value, and returns a second prediction result to the medical information system service interface program.

Further, the weaning-related medical data is cleaned and transformed by modifying any part of the weaning-related medical data that is not of a standard data type to make the part be of the standard data type. Furthermore, the part not of the standard data type includes data or a combination of data that are incomplete, noisy, duplicate, having error because of lack of examination when entered, in wrong formats, null or having unit inconsistency across different assays.

Further, the at least one algorithm is selected from Random Forest, Support Vector Machines (SVM), K Nearest Neighbor (KNN), Multilayer Perceptron (MLP), Light Gradient Boosting Machine (LightGBM), eXtreme Gradient Boosting (XGBoost), and Logistic Regression. Furthermore, during the model training based on AI learning, the weaning-related medical data is divided into a training set and a testing set, wherein 70% of the weaning-related medical data are used for the training set while 30% are used for the testing set, and the testing set is used for validation.

Further, the step of acquiring a prediction model is obtaining a plurality of prediction models as a result of the model training, in which each of the prediction models is separately obtained by using a respective algorithm to perform model training based on AI learning. The weaning prediction service program conducts prediction based on the success probabilities predicted by one of the prediction models which has a best validation result, or alternatively, based on an average value of the success probabilities predicted by all the prediction models.

The present invention further provides a ventilator-weaning timing prediction system built using the foregoing method. The system comprises:
  a server host, having the big data database, the server host being connected to the medical information system, and the server host and the medical information system jointly being connected to the medical database, in which the server host provides the medical information system service interface program to the medical information system, and executes the feature value capturing service program and the weaning prediction service program.

Further, the system has a physiological monitor connected to the medical database.

The present invention further provides a program product, being an application configured to be loaded into a computer, so as to be built as the foregoing ventilator-weaning timing prediction system.

The present invention further provides a method for using the ventilator-weaning timing prediction system. The method comprises:
  having the medical information system call for the medical information system service interface program; having the feature value capturing service program capture the medical feature value of the ventilator-using patient from the medical database; having the weaning prediction service program conduct prediction using the prediction model according to the medical feature value; and returning the prediction result to the medical information system service interface program.

Further, the method comprises acquiring the medical feature value of the ventilator-using patient in a real-time manner using a physiological monitor, so as to enable the weaning prediction service program to conduct prediction continuously.

With the foregoing technical features, the present invention has the following advantages:

1. The inventors of the present invention, after extensively studying literatures and physicians' clinical experience, have identified factors that have influence on the timing for ventilator-using patients to wean from mechanical ventilation, including a patient's age, disease severity, ventilator parameters and physiological sign parameters, and consider these factors as feature variables for AI learning, so as to use AI-based technology to predict a timing for the ventilator-using patient to receive ventilator-weaning. This allows a physician to make informed determination about the best timing for a ventilator-using patient to wean from mechanical ventilation, thereby contributing to accelerated recovery of the patient's lung respiratory function.

2. During AI learning of the present invention, 70% of the weaning-related medical data are used for the training set, while 30% are used for the testing set, and the testing set is used for validation. The prediction accuracy, sensitivity, specificity, and AUC were all high in the conducted experiment and the physician satisfaction was high for clinical use.

3. The present invention further uses a physiological monitor to acquire the ventilator-using patient's physiological data related to the medical feature values in a real-time manner, so that the weaning prediction service program can conduct prediction continuously. This advantage helps the physician to determine if the ventilator-using patient is ready for try-weaning or complete-weaning timely.

4. In the present invention, the weaning prediction service program may conduct prediction based on the success probabilities predicted by one of the prediction models which has the best validation result or, alternatively, based on an average value of the success probabilities predicted by all the prediction models, thereby making the AI-based prediction more accurate.

BRIEF DESCRIPTION OF THE DRAWINGS

FIG. 5 is a schematic view of a medical information system service interface program connected to a server host of a medical information system according to one embodiment of the present invention.

FIG. 6 is a schematic view of the medical information system service interface program of the server host, showing a first prediction result for try-weaning timings of a ventilator-using patient.

FIG. 7 is a schematic view of the medical information system service interface program of the server host, showing a first prediction result for complete-weaning timings of the ventilator-using patient.

FIG. 9 demonstrates how medical staff can adjust the ventilator-using patient's medical feature values to verify the second prediction result for potential complete-weaning.

FIG. 10 is a graph showing the first prediction results for try-weaning obtained by continuously monitoring the ventilator-using patient's physiological data related to the medical feature values using a physiological monitor.

FIG. 11 is a graph showing the second prediction results for complete-weaning obtained by continuously monitoring the ventilator-using patient's physiological data related to the medical feature values using the physiological monitor.

DETAILED DESCRIPTION OF THE INVENTION

With the aforementioned technical features, the ventilator-weaning timing prediction system, the program product thereof and the methods for building and using the same according to the present invention will be further explained below with reference to some particular embodiments.

Figure 1:
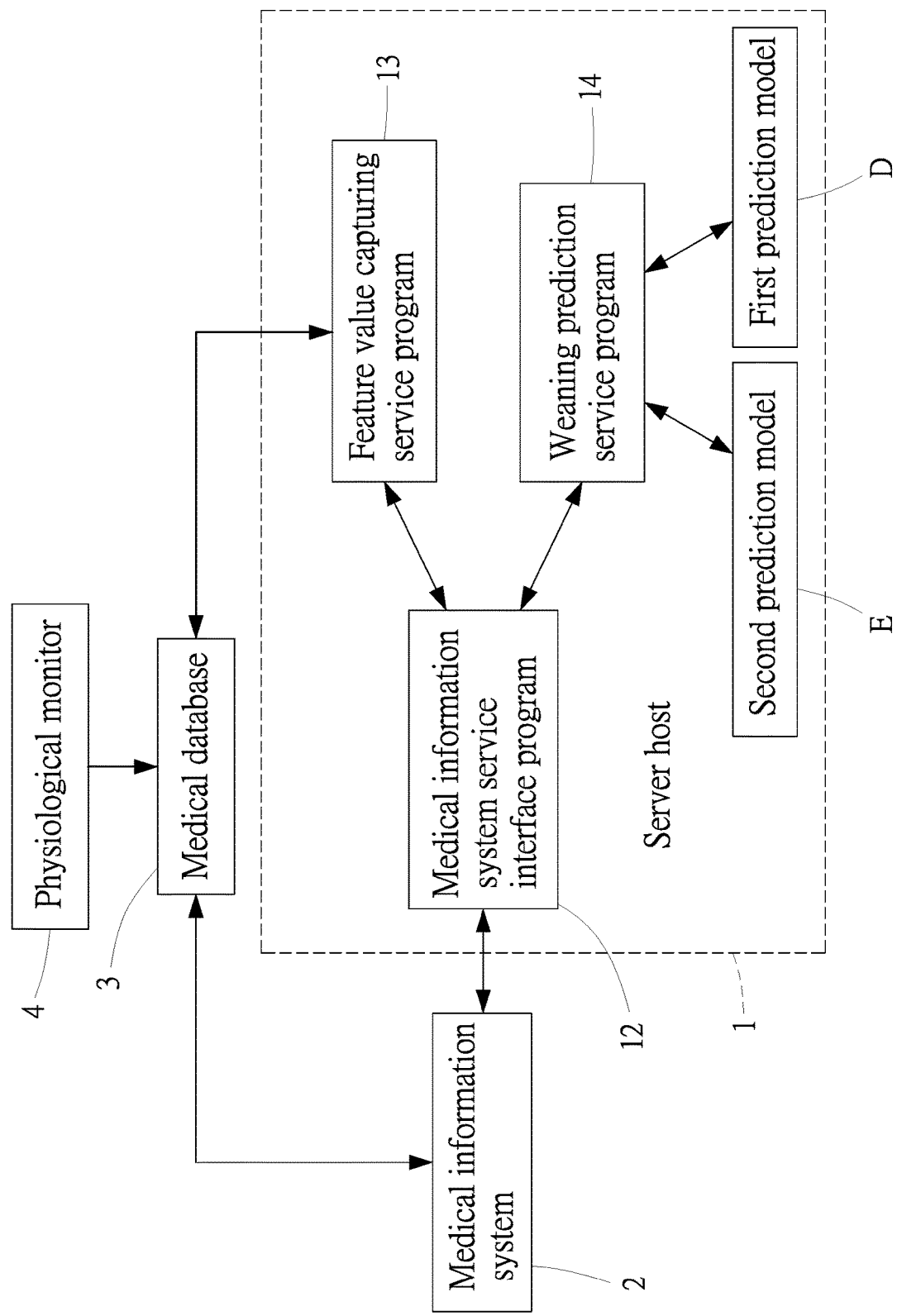
FIG. 1 is a structural diagram of a ventilator-weaning timing prediction system according to one embodiment of the present invention.
Figure 2:
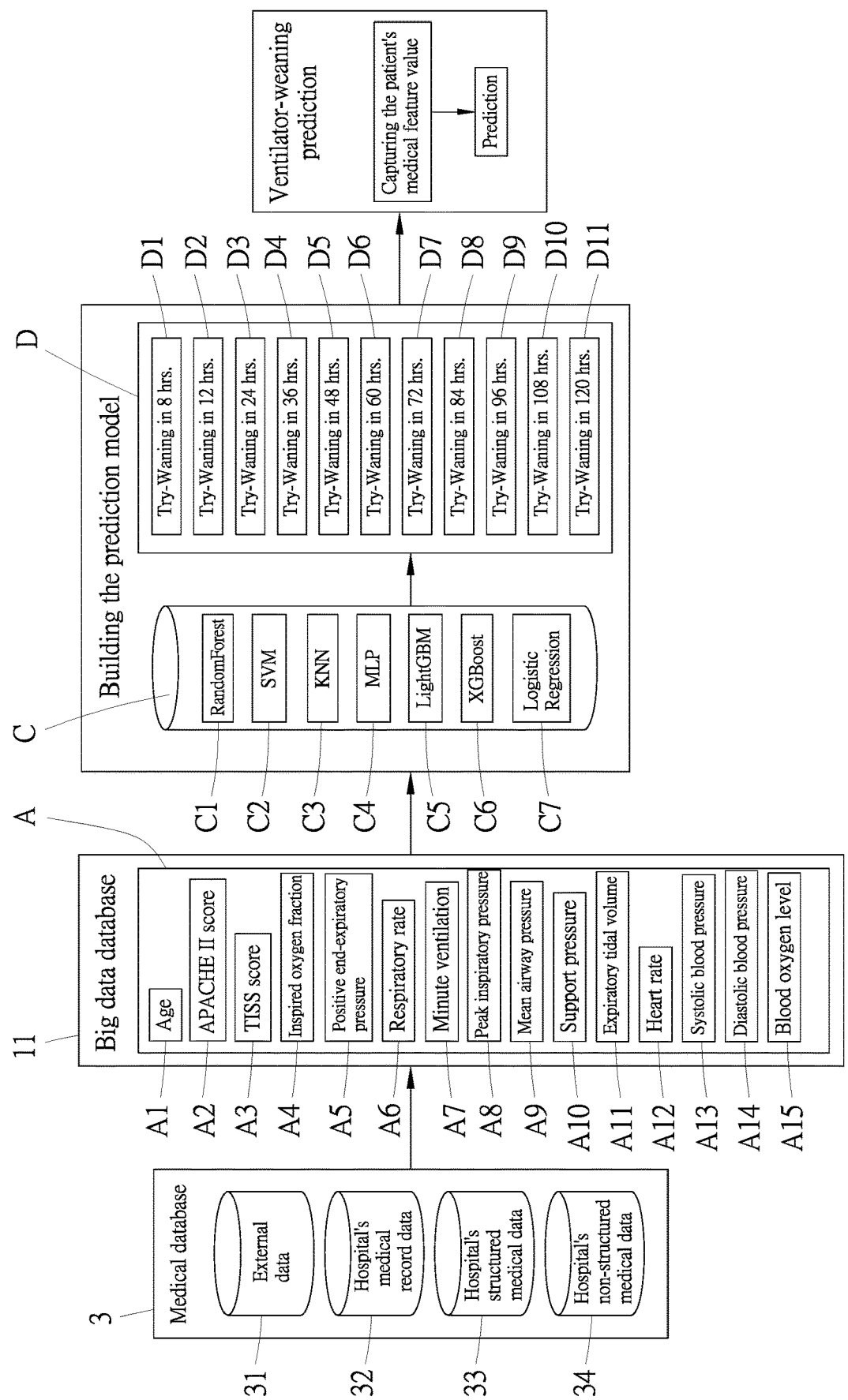
FIG. 2 is a schematic block diagram illustrating building of a ventilator try-weaning timing prediction system and how the system conducts prediction according to one embodiment of the present invention.
Figure 3:
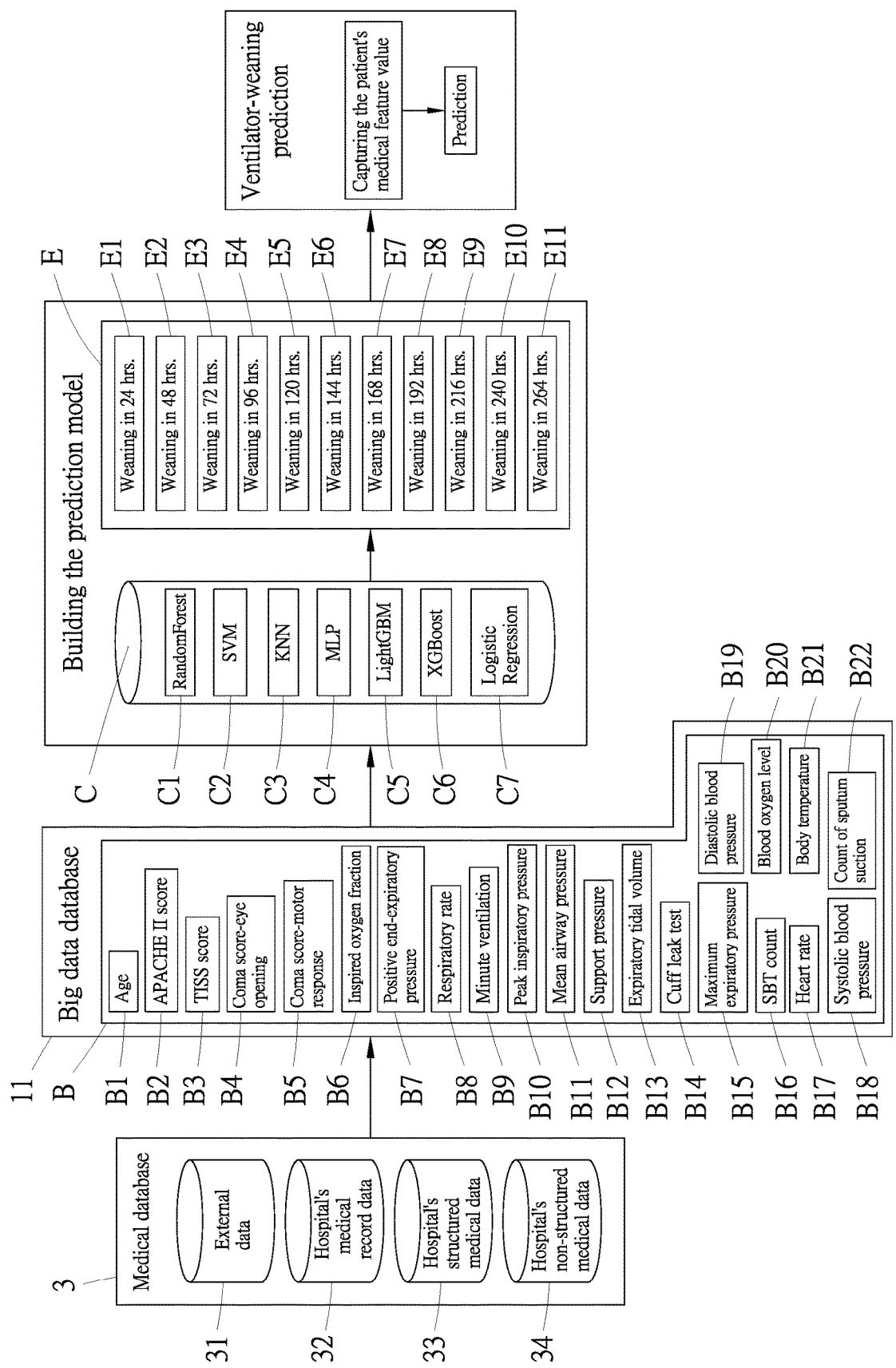
FIG. 3 is a schematic block diagram illustrating building of a ventilator complete-weaning timing prediction system and how the system conducts prediction according to one embodiment of the present invention.

Referring to FIG. 1 through FIG. 3, in the depicted embodiment, a ventilator-weaning timing prediction system comprises a server host 1 that is used for AI-based prediction. The server host 1 has a big data database 11 and is providing with a medical information system service interface program 12, a feature value capturing service program 13, and a weaning prediction service program 14. The server host 1 is connected to a medical information system 2 maintained by a medical facility. Moreover, the server host 1 and the medical information system 2 are together connected to a medical database 3.

Referring to FIG. 1, FIG. 2 and FIG. 3, the disclosed ventilator-weaning timing prediction system is used to predict try-weaning timing and a complete-weaning timing for a ventilator-using patient. Building of the ventilator-weaning timing prediction system is begun with building the server host 1, which is realized through the following steps.

In a step of acquiring weaning-related medical data, the weaning-related medical data is captured among original data stored in a medical database 3. The medical database 3 may include data from external data 31 such as the NHI research database, the HPA mortality data, and health screen examination; from medical record data 32 from individual hospitals, structured medical data 33 from individual hospitals, and non-structured medical data 34 from individual hospitals such as imaging data, radiology, text and other information about respiratory care. In one example, the ventilator-weaning-related medical data were collected from the Headquarters, the Liouying Branch, and the Jiali Branch of Chi Mei Medical Center (Taiwan) in the period between 2016 and 2019 for ventilator-using patients, with 5,500 entries were collected in total.

When any part of the ventilator-weaning-related medical data is not of a standard data type. The part is first cleaned and transformed to be of the standard data type. The part not of the standard data type may include data or a combination of data that are incomplete, noisy, duplicate, having error because of lack of examination when entered, in wrong formats, null or having unit inconsistency across different assays. Cleaning and transformation the ventilator-weaning-related medical data may include setting nulls in any incomplete data as to be ignored in the subsequent AI-based training stage.

Then a step of performing model training based on AI learning is performed as below. First, a model for prediction of try-weaning timings is trained.

A plurality of feature variables A related to try-weaning timings is extracted from the ventilator-weaning-related medical data and stored into the big data database 11. Then at least one algorithm is used to perform AI-based model training according to these feature variables A.

Selection of the feature variables A may be made according to expert experience, the clinical experience gained by physicians in the Chi Mei Hospital, or the internationally recognized literatures such as the WEANSNOW Score (Wake, Electrolytes, Acidosis/Alkalosis, Neuromuscular, Suctioning/Secretions, Nutritionally intact, Obstruction, Weaning parameters). These feature variables A may include the patient's age A1, disease severity, ventilator parameters and physiological sign parameters. Therein, disease severity includes a score obtained using the Acute Physiology and Chronic Health Evaluation II (APACHE II) A2, and a score measured using a Therapeutic Intervention Scoring System (TISS) A3. The ventilator parameters include the patient's inspired oxygen fraction A4, positive end-expiratory pressure A5, respiratory rate A6, minute ventilation A7, peak inspiratory pressure A8, mean airway pressure A9, support pressure A10, and expiratory tidal volume A11. The patient's physiological sign parameters include the patient's heart rate A12, systolic blood pressure A13, diastolic blood pressure A14, and blood oxygen level A15.

The feature variables A are then statistically classified using AI learning. AI learning in the present embodiment involves may use at least one of seven algorithms C, namely Random Forest C1, SVM C2 (Support Vector Machines), KNN C3 (K Nearest Neighbor), MLP C4 (Multilayer Perceptron), Light GBM C5 (Light Gradient Boosting Machine), XGBoost C6 (eXtreme Gradient Boosting), and Logistic Regression C7, thereby obtaining at least one prediction model. During the model training based on AI learning, the weaning-related medical data are divided into a training set and a testing set, wherein 70% of the weaning-related medical data is used for the training set, while 30% is used for the testing set. The testing set is used for validation. Referring to Table 1 through Table 12 below, as demonstrated by the results of the foregoing AI learning and validation, in the discussed example, the system performed well, with averages scores for prediction accuracy, sensitivity, specificity and AUC (Area Under the Curve) all as high as about 70% to 90%. Preferably, a plurality of prediction models are obtained as a result of the model training, in which each prediction model is separately obtained by using a respective algorithm to perform model training based on AI learning, and the weaning prediction service program 14 conducts prediction based on the probabilities of success predicted by one of the prediction models having a best validation result (such as the one having the greatest AUC), or alternatively, based on an average value of the probabilities of success predicted by all the prediction models.

TABLE 1

Predicted probability of success for try-weaning in 8 hours

| Algorithm | Accuracy | Sensitivity | Specificity | AUC |
|---|---|---|---|---|
| Logistic Regression | 0.826 | 0.805 | 0.831 | 0.893 |
| Random Forest | 0.851 | 0.850 | 0.852 | 0.938 |
| SVM | 0.814 | 0.796 | 0.818 | 0.878 |
| KNN | 0.780 | 0.856 | 0.763 | 0.868 |
| LightGBM | 0.884 | 0.880 | 0.884 | 0.953 |
| MLP | 0.901 | 0.847 | 0.913 | 0.943 |
| XGBoost | 0.884 | 0.883 | 0.884 | 0.951 |

TABLE 2

Predicted probability of success for try-weaning in 12 hours

| Algorithm | Accuracy | Sensitivity | Specificity | AUC |
|---|---|---|---|---|
| Logistic Regression | 0.730 | 0.750 | 0.723 | 0.815 |
| Random Forest | 0.779 | 0.807 | 0.769 | 0.880 |
| SVM | 0.721 | 0.725 | 0.720 | 0.798 |
| KNN | 0.704 | 0.779 | 0.676 | 0.788 |
| LightGBM | 0.813 | 0.813 | 0.813 | 0.907 |
| MLP | 0.776 | 0.775 | 0.776 | 0.877 |
| XGBoost | 0.801 | 0.800 | 0.801 | 0.897 |

TABLE 3

Predicted probability of success for try-weaning in 24 hours

| Algorithm | Accuracy | Sensitivity | Specificity | AUC |
|---|---|---|---|---|
| Logistic Regression | 0.730 | 0.730 | 0.730 | 0.796 |
| Random Forest | 0.772 | 0.800 | 0.745 | 0.857 |
| SVM | 0.722 | 0.722 | 0.722 | 0.786 |
| KNN | 0.669 | 0.756 | 0.588 | 0.743 |
| LightGBM | 0.820 | 0.823 | 0.818 | 0.893 |
| MLP | 0.738 | 0.738 | 0.738 | 0.833 |
| XGBoost | 0.808 | 0.808 | 0.808 | 0.885 |

TABLE 4

Predicted probability of success for try-weaning in 36 hours

| Algorithm | Accuracy | Sensitivity | Specificity | AUC |
|---|---|---|---|---|
| Logistic Regression | 0.721 | 0.722 | 0.721 | 0.797 |
| Random Forest | 0.783 | 0.846 | 0.711 | 0.861 |
| SVM | 0.713 | 0.713 | 0.713 | 0.776 |
| KNN | 0.683 | 0.763 | 0.593 | 0.748 |
| LightGBM | 0.791 | 0.820 | 0.758 | 0.883 |
| MLP | 0.760 | 0.810 | 0.703 | 0.845 |
| XGBoost | 0.795 | 0.825 | 0.760 | 0.873 |

TABLE 5

Predicted probability of success for try-weaning in 48 hours

| Algorithm | Accuracy | Sensitivity | Specificity | AUC |
|---|---|---|---|---|
| Logistic Regression | 0.701 | 0.700 | 0.702 | 0.775 |
| Random Forest | 0.754 | 0.754 | 0.755 | 0.839 |
| SVM | 0.709 | 0.710 | 0.709 | 0.770 |
| KNN | 0.677 | 0.746 | 0.573 | 0.723 |
| LightGBM | 0.777 | 0.777 | 0.777 | 0.861 |
| MLP | 0.735 | 0.735 | 0.735 | 0.828 |
| XGBoost | 0.763 | 0.763 | 0.763 | 0.848 |

TABLE 6 predicted probability of success for try-weaning in 60 hours

| Algorithm | Accuracy | Sensitivity | Specificity | AUC |
|---|---|---|---|---|
| Logistic Regression | 0.710 | 0.710 | 0.710 | 0.776 |
| Random Forest | 0.760 | 0.760 | 0.760 | 0.847 |
| SVM | 0.716 | 0.778 | 0.609 | 0.759 |
| KNN | 0.686 | 0.749 | 0.578 | 0.730 |
| LightGBM | 0.768 | 0.788 | 0.733 | 0.860 |
| MLP | 0.736 | 0.752 | 0.707 | 0.820 |
| XGBoost | 0.774 | 0.806 | 0.718 | 0.853 |

TABLE 7 predicted probability of success for try-weaning in 72 hours

| Algorithm | Accuracy | Sensitivity | Specificity | AUC |
|---|---|---|---|---|
| Logistic Regression | 0.739 | 0.790 | 0.633 | 0.775 |
| Random Forest | 0.747 | 0.761 | 0.720 | 0.829 |
| SVM | 0.726 | 0.781 | 0.614 | 0.759 |
| KNN | 0.663 | 0.691 | 0.607 | 0.706 |
| LightGBM | 0.761 | 0.761 | 0.760 | 0.848 |
| MLP | 0.735 | 0.729 | 0.747 | 0.810 |
| XGBoost | 0.741 | 0.741 | 0.740 | 0.828 |

TABLE 8

Predicted probability of success for try-weaning in 84 hours

| Algorithm | Accuracy | Sensitivity | Specificity | AUC |
|---|---|---|---|---|
| Logistic Regression | 0.712 | 0.712 | 0.712 | 0.775 |
| Random Forest | 0.765 | 0.784 | 0.720 | 0.827 |
| SVM | 0.723 | 0.781 | 0.587 | 0.737 |
| KNN | 0.660 | 0.699 | 0.568 | 0.686 |
| LightGBM | 0.751 | 0.750 | 0.752 | 0.842 |
| MLP | 0.720 | 0.720 | 0.720 | 0.800 |
| XGBoost | 0.762 | 0.763 | 0.759 | 0.844 |

TABLE 9

Predicted probability of success for try-weaning in 96 hours

| Algorithm | Accuracy | Sensitivity | Specificity | AUC |
|---|---|---|---|---|
| Logistic Regression | 0.711 | 0.711 | 0.711 | 0.781 |
| Random Forest | 0.740 | 0.740 | 0.741 | 0.821 |
| SVM | 0.707 | 0.706 | 0.707 | 0.771 |
| KNN | 0.671 | 0.717 | 0.550 | 0.700 |
| LightGBM | 0.752 | 0.752 | 0.751 | 0.843 |
| MLP | 0.738 | 0.738 | 0.738 | 0.815 |
| XGBoost | 0.762 | 0.783 | 0.705 | 0.836 |

TABLE 10

Predicted probability of success for try-weaning in 108 hours

| Algorithm | Accuracy | Sensitivity | Specificity | AUC |
|---|---|---|---|---|
| Logistic Regression | 0.743 | 0.783 | 0.629 | 0.785 |
| Random Forest | 0.766 | 0.782 | 0.718 | 0.842 |
| SVM | 0.736 | 0.789 | 0.580 | 0.748 |
| KNN | 0.666 | 0.693 | 0.587 | 0.696 |
| LightGBM | 0.755 | 0.755 | 0.753 | 0.846 |
| MLP | 0.743 | 0.755 | 0.707 | 0.815 |
| XGBoost | 0.761 | 0.777 | 0.713 | 0.829 |

TABLE 11

Predicted probability of success for try-weaning in 120 hours

| Algorithm | Accuracy | Sensitivity | Specificity | AUC |
|---|---|---|---|---|
| Logistic Regression | 0.733 | 0.733 | 0.734 | 0.810 |
| Random Forest | 0.773 | 0.773 | 0.773 | 0.861 |
| SVM | 0.758 | 0.805 | 0.602 | 0.778 |
| KNN | 0.679 | 0.709 | 0.578 | 0.694 |
| LightGBM | 0.767 | 0.767 | 0.768 | 0.864 |
| MLP | 0.715 | 0.700 | 0.763 | 0.826 |
| XGBoost | 0.763 | 0.763 | 0.763 | 0.856 |

A step of acquiring a prediction model then follows.

According to the foregoing model training, at least one first prediction model D is obtained for AI-based prediction about timings for a ventilator-using patient to receive try-weaning. The at least one first prediction model D includes 11 versions, for try-weaning in 8 hours D1, try-weaning in 12 hours D2, try-weaning in 24 hours D3, try-weaning in 36 hours D4, try-weaning in 48 hours D5, try-weaning in 60 hours D6, try-weaning in 72 hours D7, try-weaning in 84 hours D8, try-weaning in 96 hours D9, try-weaning in 108 hours D10, try-weaning in 120 hours D11, respectively.

Then is a step of building web-based services.

After the at least one first prediction model D is obtained, the medical information system service interface program 12, the feature value capturing service program 13 and the weaning prediction service program 14 required by the AI-based prediction are built into a program product that loads an application into a computer acting as the server host 1. The server host 1 so set up is then connected to the medical information system 2 of the medical facility and the foregoing medical database 3.

Model training for complete-weaning timings is done similarly. Particularly, a plurality of feature variables B related to timings for complete ventilator-weaning is extracted from the ventilator-weaning-related medical data and stored into the big data database 11. Then AI-based model training can be performed using these feature variables B to obtain at least one second prediction model E.

Therein, the feature variables B can also include the patient's age B1, disease severity, ventilator parameters and physiological sign parameters. Therein, disease severity includes a score obtained using the Acute Physiology and Chronic Health Evaluation II (APACHE II) B2, a score measured using a Therapeutic Intervention Scoring System (TISS) B3, coma score-eye opening B4, and coma score-motor response B5. The ventilator parameters include the patient's inspired oxygen fraction B6, positive end-expiratory pressure B7, respiratory rate B8, minute ventilation B9, peak inspiratory pressure B10, mean airway pressure B11, support pressure B12, expiratory tidal volume B13, cuff leak test B14, maximum expiratory pressure B15, and a count of spontaneous breathing trials (SBT) B16. The patient's physiological sign parameters include the patient's heart rate B17, systolic blood pressure B18, diastolic blood pressure B19, blood oxygen level B20, body temperature B21, and a count of sputum suction B22.

Referring to Table 1 through Table 11 below, as demonstrated by the results of the foregoing AI learning and validation, in the discussed example, the system performed well, with averages scores for prediction accuracy, sensitivity, specificity and AUC (Area Under the Curve) all as high as about 70% to 90%. Preferably, a plurality of prediction models are obtained as a result of the model training, in which each prediction model is separately obtained by using a respective algorithm to perform model training based on AI learning, and the weaning prediction service program 14 conducts prediction based on the probabilities of success predicted by one of the prediction models having a best validation result (such as the one having the greatest AUC), or alternatively, based on an average value of the probabilities of success predicted by all the prediction models.

TABLE 1

Predicted probability of success for weaning in 24 hours

| Algorithm | Accuracy | Sensitivity | Specificity | AUC |
|---|---|---|---|---|
| Logistic Regression | 0.845 | 0.843 | 0.845 | 0.909 |
| Random Forest | 0.837 | 0.843 | 0.835 | 0.900 |
| SVM | 0.672 | 0.675 | 0.671 | 0.720 |
| KNN | 0.619 | 0.602 | 0.623 | 0.638 |
| LightGBM | 0.817 | 0.819 | 0.816 | 0.882 |
| MLP | 0.832 | 0.831 | 0.832 | 0.908 |
| XGBoost | 0.792 | 0.783 | 0.794 | 0.878 |

TABLE 2

Predicted probability of success for weaning in 48 hours

| Algorithm | Accuracy | Sensitivity | Specificity | AUC |
|---|---|---|---|---|
| Logistic Regression | 0.825 | 0.833 | 0.821 | 0.909 |
| Random Forest | 0.822 | 0.825 | 0.821 | 0.905 |
| SVM | 0.644 | 0.714 | 0.612 | 0.724 |
| KNN | 0.559 | 0.627 | 0.527 | 0.611 |
| LightGBM | 0.832 | 0.833 | 0.832 | 0.911 |
| MLP | 0.812 | 0.810 | 0.813 | 0.878 |
| XGBoost | 0.845 | 0.841 | 0.846 | 0.908 |

TABLE 3

Predicted probability of success for weaning in 72 hours

| Algorithm | Accuracy | Sensitivity | Specificity | AUC |
|---|---|---|---|---|
| Logistic Regression | 0.792 | 0.793 | 0.791 | 0.880 |
| Random Forest | 0.800 | 0.810 | 0.791 | 0.890 |
| SVM | 0.654 | 0.655 | 0.653 | 0.711 |
| KNN | 0.546 | 0.529 | 0.560 | 0.607 |
| LightGBM | 0.769 | 0.770 | 0.769 | 0.866 |
| MLP | 0.767 | 0.793 | 0.747 | 0.857 |
| XGBoost | 0.794 | 0.787 | 0.800 | 0.874 |

TABLE 4

Predicted probability of success for weaning in 96 hours

| Algorithm | Accuracy | Sensitivity | Specificity | AUC |
|---|---|---|---|---|
| Logistic Regression | 0.807 | 0.808 | 0.806 | 0.891 |
| Random Forest | 0.794 | 0.803 | 0.785 | 0.885 |
| SVM | 0.654 | 0.702 | 0.602 | 0.722 |
| KNN | 0.589 | 0.635 | 0.539 | 0.634 |
| LightGBM | 0.787 | 0.784 | 0.791 | 0.884 |
| MLP | 0.812 | 0.817 | 0.806 | 0.889 |
| XGBoost | 0.802 | 0.803 | 0.801 | 0.866 |

TABLE 5

Predicted probability of success for weaning in 120 hours

| Algorithm | Accuracy | Sensitivity | Specificity | AUC |
|---|---|---|---|---|
| Logistic Regression | 0.815 | 0.817 | 0.811 | 0.905 |
| Random Forest | 0.817 | 0.817 | 0.817 | 0.906 |
| SVM | 0.719 | 0.723 | 0.713 | 0.778 |
| KNN | 0.637 | 0.591 | 0.701 | 0.678 |
| LightGBM | 0.815 | 0.813 | 0.817 | 0.896 |
| MLP | 0.792 | 0.791 | 0.793 | 0.886 |
| XGBoost | 0.817 | 0.817 | 0.817 | 0.895 |

TABLE 6 predicted probability of success for weaning in 144 hours

| Algorithm | Accuracy | Sensitivity | Specificity | AUC |
|---|---|---|---|---|
| Logistic Regression | 0.805 | 0.805 | 0.804 | 0.888 |
| Random Forest | 0.805 | 0.805 | 0.804 | 0.889 |
| SVM | 0.652 | 0.652 | 0.650 | 0.713 |
| KNN | 0.596 | 0.559 | 0.664 | 0.637 |
| LightGBM | 0.777 | 0.777 | 0.776 | 0.864 |
| MLP | 0.800 | 0.840 | 0.727 | 0.872 |
| XGBoost | 0.792 | 0.813 | 0.755 | 0.870 |

TABLE 7

Predicted probability of success for weaning in 168 hours

| Algorithm | Accuracy | Sensitivity | Specificity | AUC |
|---|---|---|---|---|
| Logistic Regression | 0.800 | 0.814 | 0.767 | 0.881 |
| Random Forest | 0.797 | 0.803 | 0.783 | 0.877 |
| SVM | 0.699 | 0.713 | 0.667 | 0.725 |
| KNN | 0.624 | 0.634 | 0.600 | 0.657 |
| LightGBM | 0.797 | 0.810 | 0.767 | 0.875 |
| MLP | 0.797 | 0.803 | 0.783 | 0.872 |
| XGBoost | 0.769 | 0.767 | 0.775 | 0.866 |

TABLE 8

Predicted probability of success for weaning in 192 hours

| Algorithm | Accuracy | Sensitivity | Specificity | AUC |
|---|---|---|---|---|
| Logistic Regression | 0.792 | 0.820 | 0.712 | 0.875 |
| Random Forest | 0.805 | 0.807 | 0.798 | 0.881 |
| SVM | 0.702 | 0.702 | 0.702 | 0.769 |
| KNN | 0.612 | 0.593 | 0.663 | 0.672 |
| LightGBM | 0.794 | 0.803 | 0.769 | 0.872 |
| MLP | 0.772 | 0.769 | 0.779 | 0.870 |
| XGBoost | 0.800 | 0.803 | 0.788 | 0.865 |

TABLE 9

Predicted probability of success for weaning in 216 hours

| Algorithm | Accuracy | Sensitivity | Specificity | AUC |
|---|---|---|---|---|
| Logistic Regression | 0.807 | 0.807 | 0.806 | 0.876 |
| Random Forest | 0.802 | 0.801 | 0.806 | 0.874 |
| SVM | 0.704 | 0.709 | 0.688 | 0.751 |
| KNN | 0.657 | 0.673 | 0.602 | 0.660 |
| LightGBM | 0.827 | 0.853 | 0.742 | 0.870 |
| MLP | 0.807 | 0.807 | 0.806 | 0.880 |
| XGBoost | 0.777 | 0.775 | 0.785 | 0.868 |

TABLE 10

Predicted probability of success for weaning in 240 hours

| Algorithm | Accuracy | Sensitivity | Specificity | AUC |
|---|---|---|---|---|
| Logistic Regression | 0.807 | 0.813 | 0.786 | 0.894 |
| Random Forest | 0.832 | 0.832 | 0.833 | 0.892 |
| SVM | 0.682 | 0.683 | 0.679 | 0.772 |
| KNN | 0.649 | 0.641 | 0.679 | 0.723 |
| LightGBM | 0.802 | 0.806 | 0.786 | 0.885 |
| MLP | 0.784 | 0.784 | 0.786 | 0.887 |
| XGBoost | 0.802 | 0.800 | 0.810 | 0.877 |

TABLE 11

Predicted probability of success for weaning in 264 hours

| Algorithm | Accuracy | Sensitivity | Specificity | AUC |
|---|---|---|---|---|
| Logistic Regression | 0.820 | 0.820 | 0.818 | 0.909 |
| Random Forest | 0.805 | 0.804 | 0.805 | 0.905 |
| SVM | 0.694 | 0.702 | 0.662 | 0.746 |
| KNN | 0.662 | 0.680 | 0.584 | 0.660 |
| LightGBM | 0.822 | 0.820 | 0.831 | 0.908 |
| MLP | 0.759 | 0.752 | 0.792 | 0.879 |
| XGBoost | 0.817 | 0.817 | 0.818 | 0.913 |

According to the foregoing model training, at least one second prediction model E is obtained for AI-based prediction about timings for a ventilator-using patient to receive complete-weaning. The at least one second prediction model E includes 11 versions, for weaning in 24 hours E1, weaning in 48 hours E2, weaning in 72 hours E3, weaning in 96 hours E4, weaning in 120 hours E5, weaning in 144 hours E6, weaning in 168 hours E7, weaning in 192 hours E8, weaning in 216 hours E9, weaning in 240 hours E10, weaning in 264 hours E11, respectively.

Figure 4:
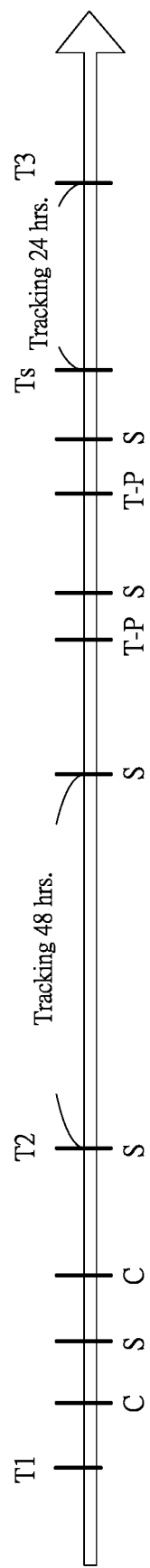
FIG. 4 is a timeline showing a timing sequence along which a patient uses a ventilator, carries out try-weaning timing and completely weans from the ventilator according to one embodiment of the present invention.

Referring to FIG. 4, it is to be further noted that in the context of the AI training, a timing for a ventilator-using patient to have successful try-weaning refers a time point at which the ventilator is switched from the control mode c to the support mode s and stays in the control mode c for 48 hours. Thus, for a ventilator-using patient starting to use a ventilator at a time point T1, if the ventilator is once switched from the control mode c to the support modes, but is switched back to the control mode c in the next 48 hours because of the patient's need, this time of try-weaning is failed. If the ventilator is switched from the control mode c to the support modes again at a later time point T2, and this time stays in the support modes for 48 hours, the time point T2 is regarded as the timing for the ventilator-using patient's successful try-weaning. The window for counting the times of spontaneous breathing trials (SBT) B16 covers the count of SBTs in the period between when the ventilator-using patient successfully passes the try-weaning started from the time point T2 and when the ventilator-using patient successfully passes the complete weaning started at a time point T3. The window for counting times of sputum suction B22 covers the count of sputum suction in the period between when the ventilator-using patient successfully passes the complete weaning started at the time point T3 and a time point Ts which is 24 hours earlier than T3.

Figure 5:
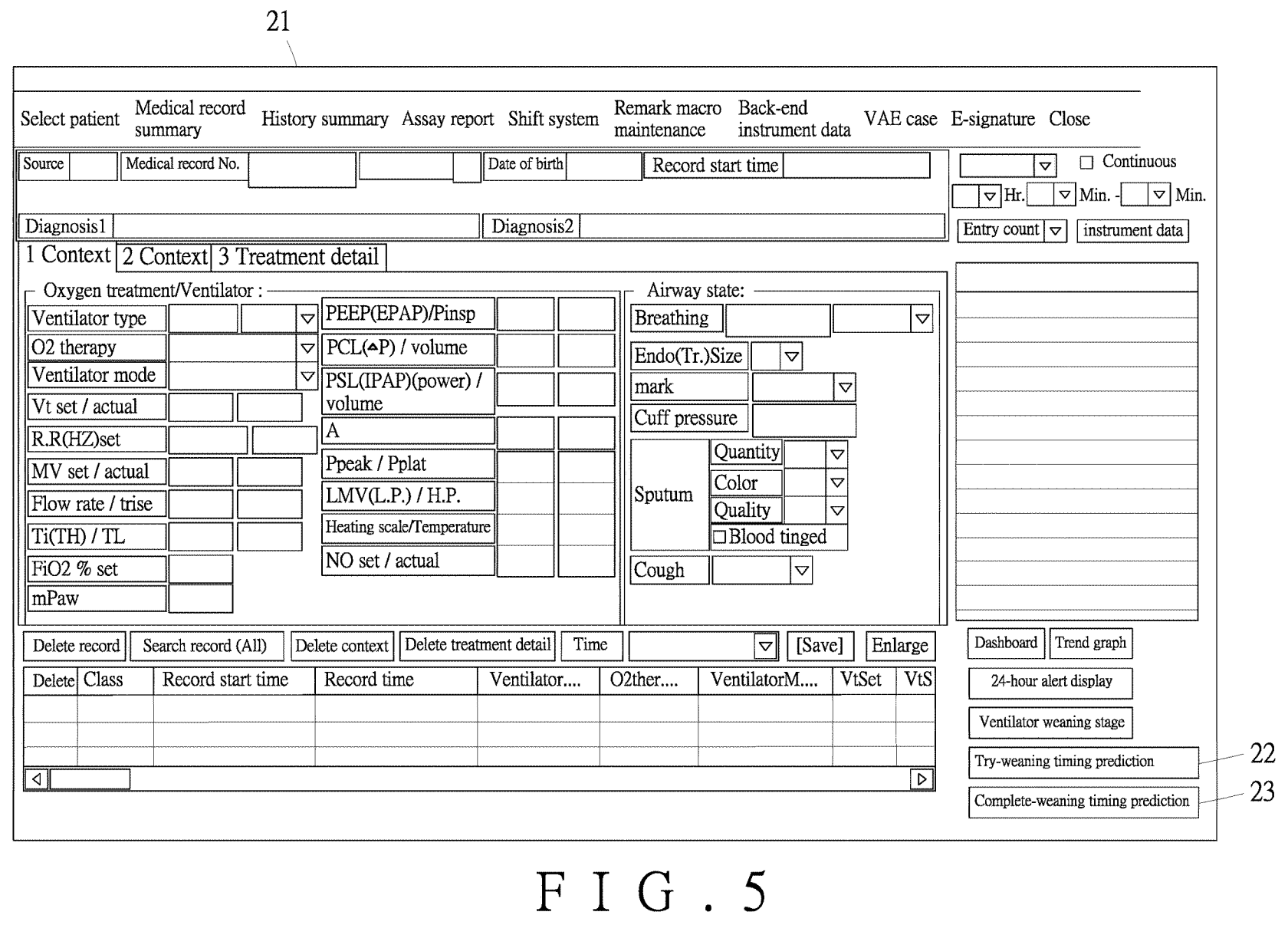

Referring to FIG. 1, FIG. 5 and FIG. 6, the physician enters the medical information about the ventilator-using patient into the medical information system 2 of the medical facility through a medical record interface 21. The medical data are stored in the relevant medical database 3. In the medical record interface 21, a first link instruction 22 for try-weaning timing prediction and a second link instruction 23 for complete-weaning timing prediction are provided. When instructing the patient to use mechanical ventilation, the physician may click on the first link instruction 22 to have the medical information system 2 call for the medical information system service interface program 12. At this time, the medical information system service interface program 12 is shown in the physician's clinic computer, and the computer executes the feature value capturing service program 13 and the weaning prediction service program 14. The feature value capturing service program 13 captures the medical feature values of the ventilator-using patient related to the foregoing feature variables A from the relevant medical database 3. Then the weaning prediction service program 14 conducts prediction using the first prediction model D according to the medical feature values, and returns a first prediction result to the medical information system service interface program 12, for the physician to evaluate a timing of switching the ventilator from the control mode c to the support modes for the ventilator-using patient.

Referring to FIG. 1, FIG. 5 and FIG. 7, similarly, when the ventilator-using patient enters the try-weaning stage successfully, the physician may activate the second link instruction 23 to make the medical information system 2 call for the medical information system service interface program 12. As a result, the physician's clinic computer shows the medical information system service interface program 12 and the feature value capturing service program 13 and the weaning prediction service program 14 are executed. The feature value capturing service program 13 extracts the ventilator-using patient's medical feature values related to the foregoing feature variables B from the medical data in the relevant medical database 3. Then the weaning prediction service program 14 conducts prediction according to the medical feature values using the second prediction model E, and returns a second prediction result to the medical information system service interface program 12 as a reference for the physician to evaluate the ventilator-using patient's complete-weaning.

Figure 8:
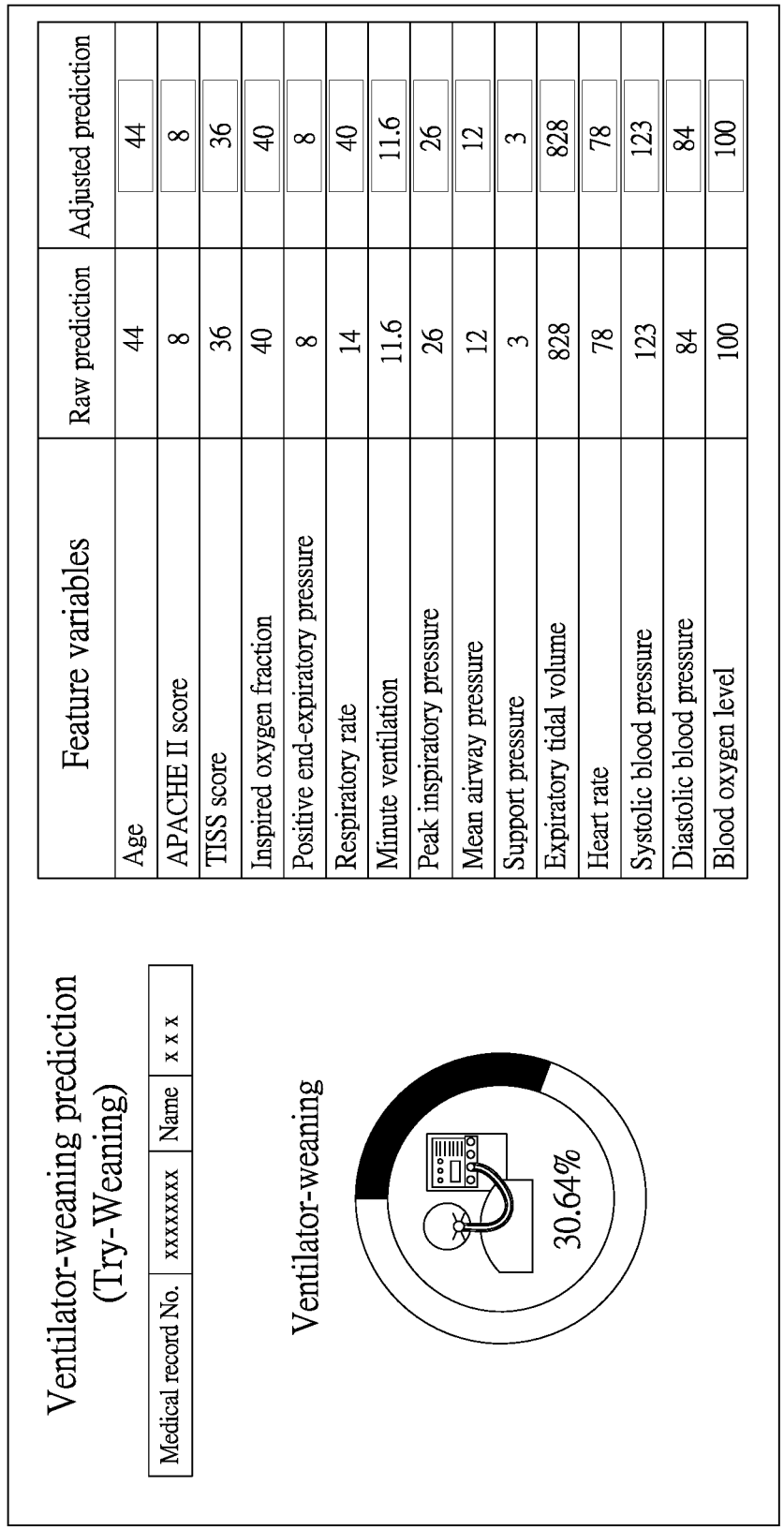
FIG. 8 demonstrates how medical staff can adjust the ventilator-using patient's medical feature values to verify the first prediction result for potential try-weaning.

Referring to FIG. 8 and FIG. 9, the medical staff may adjust the medical feature values of the ventilator-using patient to evaluate the patient's state after possible his/her try-weaning or complete-weaning. FIG. 8 and FIG. 9 show exemplary prediction for try-weaning and complete weaning in 8 hours.

In one example, after a trail use of the disclosed in ventilator-weaning timing prediction system in the Headquarters of Chi Mei Hospital in May 2020, a satisfaction survey was conducted among the ICU staff (including the physicians and the respiratory therapists) on the fifth day of June using a 5-point-scale questionnaire, and according to the 35 copies of the recovered questionnaire, the average satisfaction was 4.7 points, demonstrating the practicability of the disclosed system.

Referring to FIG. 1, FIG. 10 and FIG. 11, a physiological monitor 4, such as a sphygmomanometer, an oximeter, etc., may be additionally used to monitor a ventilator-using patient, so as to acquire the ventilator-using patient's medical data and upload to the relevant medical database 3 in a real-time manner. The feature value capturing service program 13 is configured to continuously or periodically extract the relevant medical feature values from the medical database 3 for the weaning prediction service program 14 to conduct continuous prediction. This allows the medical staff to make informed determination about the best timing for the ventilator-using patient's try-weaning or complete-weaning, thereby contributing to accelerated recovery of the patient's lung respiratory function.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A method for building and using a ventilator-weaning timing prediction system, the ventilator-weaning timing prediction system predicting a try-weaning regimen and a complete weaning regimen for a patient currently connected to a ventilator at a medical facility, the ventilator being connected to a physiological monitor, and the physiological monitor being connected to a medical database server of the medical facility, the medical database server of the medical facility including patient record data of the patient currently connected to the ventilator at the medical facility and of patients previously connected to ventilators at the medical facility, the method comprising:

providing a server host system including a big data database subsystem and a prediction model building subsystem;

connecting the big data database subsystem with the medical database server, and the big data database subsystem capturing weaning-related medical data from the patient record data of patients previously connected to ventilators at the medical facility stored in the medical database server, the big data database subsystem analyzing the captured weaning-related medical data for determining if the captured weaning-related medical data is of a standard data configuration, and upon determining that the captured weaning-related medical data is not of a standard data configuration, the big data database subsystem transforming the captured weaning-related medical data into a standard data configuration;

initiating the big data database subsystem to divide the captured weaning-related medical data in a standard data configuration into a training data set for try-weaning and a testing data set for try-weaning, and further employing the big data database subsystem to extract feature variables for try-weaning from the training data set for try-weaning, each extracted feature variable for try-weaning being a medical data parameter impacting weaning of a corresponding patient previously connected to a ventilator partially therefrom, wherein selection of the extracted feature variables for try-weaning being responsive to at least input provided by medical practitioners at the medical facility, and wherein the extracted feature variables for try-weaning include at least age, disease severity, ventilator parameters, and physiological sign parameters of a corresponding patient previously connected to a ventilator;

initiating the prediction model building subsystem to connect with the big data database subsystem and acquire the extracted feature variables for try-weaning, the training data set for try-weaning, and the testing data set for try-weaning, the prediction model building subsystem operating on the extracted feature variables for try-weaning and the training data set for try-weaning using a plurality of preselected algorithms to thereby generate respective multiple prediction weaning models for try-weaning, each prediction weaning model for try-weaning providing a probability of success of partially weaning at predetermined spans of time;

subsequent to generating the multiple prediction weaning models for try-weaning, the prediction model building subsystem validating the multiple generated prediction weaning models for try-weaning using the testing data set for try-weaning, and responsive to and in accordance with validation results of the multiple prediction weaning models for try-weaning, the prediction model building subsystem selecting at least one of the multiple prediction weaning models for try-weaning to be the first designated weaning prediction model, the first designated weaning prediction model providing success probabilities for partially weaning at the predetermined spans of time; and initiating the big data database subsystem to divide the captured weaning-related medical data in a standard data configuration into a training data set for complete weaning and a testing data set for complete weaning, and further employing the big data database subsystem to extract feature variables for complete weaning from the training data set for complete weaning, each extracted feature variable for complete weaning being a medical data parameter impacting weaning of a corresponding patient previously connected to a ventilator fully therefrom, wherein selection of the extracted feature variables for complete weaning being responsive to at least input provided by medical practitioners at the medical facility, and wherein the extracted feature variables for complete weaning include at least age, disease severity, ventilator parameters, and physiological sign parameters of a corresponding patient previously connected to a ventilator;

initiating the prediction model building subsystem to connect with the big data database subsystem and acquire the extracted feature variables for complete weaning, the training data set for complete weaning, and the testing data set for complete weaning, the prediction model building subsystem operating on the extracted feature variables for complete weaning and the training data set for complete weaning using the plurality of preselected algorithms to thereby generate respective multiple prediction weaning models for complete weaning, each prediction weaning model for complete weaning providing a probability of success of fully weaning at predetermined spans of time;

subsequent to generating the multiple prediction weaning models for complete weaning, the prediction model building subsystem validating the multiple generated prediction weaning models for complete weaning using the testing data set for complete weaning, and responsive to and in accordance with validation results of the multiple prediction weaning models for complete weaning, the prediction model building subsystem selecting at least one of the multiple prediction weaning models for complete weaning to be the second designated weaning prediction model, the second designated weaning prediction model providing success probabilities for fully weaning at the predetermined spans of time; and actuating the server host system to provide a medical information system service interface program subsystem, a feature value capturing service program subsystem, and a weaning prediction service program subsystem, connecting the medical information system service interface program subsystem with the feature value capturing service program subsystem, the weaning prediction service program subsystem, and a medical information system server of the medical facility that includes at least an input terminal and an output visual display terminal, the medical information system server being connected to the medical database server, the medical information system service interface program subsystem providing an input and an output interface between the server host system and the medical information system server;

the medical information system service interface program subsystem providing a command prompt via the input interface for the medical practitioner at the medical facility via the input terminal of the medical information system server to selectively initiate the try-weaning regimen for the patient currently connected to the ventilator at the medical facility, and the feature value capturing service program subsystem responsively connecting with the medical database server to capture the patient record data of the patient currently connected to the ventilator, and further, the feature value capturing service program subsystem extracting medical feature values relating to try-weaning from the captured patient record data of the patient currently connected to the ventilator, the extracted medical feature values relating to try-weaning of the patient currently connected to the ventilator corresponding to the feature variables for try-weaning extracted from the training data set for try-weaning, and the weaning prediction service program subsystem operating on the designated first weaning prediction model according to the extracted medical feature values relating to try-weaning of the patient currently connected to the ventilator for generating the try-weaning regimen for the patient currently connected to the ventilator, and the medical information system service interface program subsystem displaying the try-weaning regimen for the patient currently connected to the ventilator to the medical practitioner at the medical facility on the output visual display terminal of the medical information system server via the output interface, the try-weaning regimen for the patient currently connected to the ventilator including success probabilities for partially weaning the patient from the ventilator at the predetermined spans of time;

wherein the ventilator to which the patient currently is connected to is selectively operable by the medical practitioner for partially weaning the patient from the ventilator in correspondence with the try-weaning regimen displayed on the output visual display terminal of the medical information system server;

wherein when the ventilator to which the patient currently is connected to is operated on by the medical practitioner to partially wean the patient therefrom, the ventilator is selectively switched from a control mode to a support mode, and the patient being successfully try-weaned with respect the ventilator to which the patient currently is connected to only if the ventilator remains in the support mode for at least forty eight (48) hours, and if the ventilator to which the patient currently is connected to is selectively switched by the medical practitioner from the support mode back to the control mode responsive to patient record data of the patient being indicative of deteriorating health of the patient, the patient has been unsuccessfully try-weaned with respect the ventilator to which the patient currently is connected to; and subsequent to the patient currently connected to the ventilator being successfully try-weaned from the ventilator, the medical information system service interface program subsystem providing a command prompt via the input interface for the medical practitioner at the medical facility via the input terminal of the medical information system server to selectively initiate the complete weaning regimen for the patient currently connected to the ventilator at the medical facility, and the feature value capturing service program subsystem responsively connecting with the medical database server to capture the patient record data of the patient currently connected to the ventilator, and further, the feature value capturing service program subsystem extracting medical feature values relating to complete weaning from the captured patient record data of the patient currently connected to the ventilator, the extracted medical feature values relating to complete weaning of the patient currently connected to the ventilator corresponding to the feature variables for complete weaning extracted from the training data set for complete weaning, and the weaning prediction service program subsystem operating on the designated second weaning prediction model according to the extracted medical feature values relating to complete weaning of the patient currently connected to the ventilator for generating the complete weaning regimen for the patient currently connected to the ventilator, and the medical information system service interface program subsystem displaying the complete weaning regimen for the patient currently connected to the ventilator to the medical practitioner at the medical facility on the output visual display terminal of the medical information system server via the output interface, the complete weaning regimen for the patient currently connected to the ventilator including success probabilities for fully weaning the patient from the ventilator at the predetermined spans of time;

wherein the ventilator to which the patient currently is connected to is selectively operable by the medical practitioner for fully weaning the patient from the ventilator in correspondence with the complete weaning regimen displayed on the output visual display terminal of the medical information system server; and wherein with respect to the extracted medical feature values relating to try-weaning and the extracted medical feature values relating to complete weaning of the patient currently connected to the ventilator, corresponding patient record data of the patient currently connected to the ventilator is continuously captured over a predetermined period of time by the physiological monitor, and responsively, the corresponding patient record data of the patient currently connected to the ventilator is continuously updated in the medical database server, and further responsively, the feature value capturing service program subsystem continuously updates the captured patient record data of the patient currently connected to the ventilator, and the extracted medical feature values relating to try-weaning and the extracted medical feature values relating to complete weaning of the patient currently connected to the ventilator are thereby, respectively, updated on a real-time basis for operation on by the first designated weaning prediction model and the second designated weaning prediction model, and the try-weaning regimen and the complete weaning regimen for the patient currently connected to the ventilator being generated are, respectively, updated on a real-time basis, in accordance with the extracted medical feature values relating to try-weaning, and the extracted medical feature values relating to complete weaning, of the patient currently connected to the ventilator.

2. The method of claim 1, wherein the extracted feature variables for try-weaning, further, include a disease severity including a score obtained using an Acute Physiology and Chronic Health Evaluation II, a score obtained using a Therapeutic Intervention Scoring System, the ventilator parameters including inspired oxygen fraction, positive end-expiratory pressure, respiratory rate, minute ventilation, peak inspiratory pressure, mean airway pressure, support pressure, and expiratory tidal volume, with respect to the patient currently connected to the ventilator, and the physiological sign parameters of the patient currently connected to the ventilator including the patient's heart rate, systolic blood pressure, diastolic blood pressure, and blood oxygen level;

wherein with respect to the first designated weaning prediction model, the predetermined spans of time include try-weaning in 8 hours, try-weaning in 12 hours, try-weaning in 24 hours, try-weaning in 36 hours, try-weaning in 48 hours, try-weaning in 60 hours, try-weaning in 72 hours, try-weaning in 84 hours, try-weaning in 96 hours, try-weaning in 108 hours, and try-weaning in 120 hours.

3. The method of claim 2, wherein the extracted feature variables for complete weaning, further, include a disease severity including a score obtained using an Acute Physiology and Chronic Health Evaluation II, a score measured using a Therapeutic Intervention Scoring System, coma score-eye opening, and coma score-motor response, and the ventilator parameters including inspired oxygen fraction, positive end-expiratory pressure, respiratory rate, minute ventilation, peak inspiratory pressure, mean airway pressure, support pressure, expiratory tidal volume, cuff leak test, maximum expiratory pressure, and a count of spontaneous breathing trials (SBT) of the patient currently connected to the ventilator, and the physiological sign parameters including heart rate, systolic blood pressure, diastolic blood pressure, blood oxygen level, body temperature, and a count of sputum suction of the patient currently connected to the ventilator;

wherein with respect to the second designated weaning prediction model, the predetermined spans of time include complete weaning in 24 hours, complete weaning in 48 hours, complete weaning in 72 hours, complete weaning in 96 hours, complete weaning in 120 hours, complete weaning in 144 hours, complete weaning in 168 hours, complete weaning in 192 hours, complete weaning in 216 hours, complete weaning in 240 hours, and complete weaning in 264 hours.

4. The method of claim 1, wherein the captured weaning-related medical data that is not of a standard data configuration includes data that is incomplete, noisy, duplicate, having error because of lack of examination when entered, incorrectly formatted, null, or having unit inconsistency across different assays.

5. The method of claim 1, wherein the plurality of preselected algorithms include RandomForest, Support Vector Machines (SVM), K Nearest Neighbor (KNN), Multilayer Perceptron (MLP), Light Gradient Boosting Machine (LightGBM), eXtreme Gradient Boosting (XGBoost), and Logistic Regression.

6. The method of claim 1, wherein when dividing the captured weaning-related medical data in a standard data configuration into a training data set for try-weaning and complete weaning and a testing data set for try-weaning and complete weaning, 70% of the weaning-related medical data is used for the training data set for try-weaning and complete weaning, and 30% is used for the testing data set for try-weaning and complete weaning.

7. The method of claim 1, wherein when selecting at least one of the prediction weaning models for try-weaning to be the first designated weaning prediction model and when selecting at least one of the prediction weaning models for complete weaning to be the second designated weaning prediction model, the prediction weaning model for try-weaning having the most accurate validation result amongst the multiple prediction weaning models for try-weaning is selected to be the first designated weaning prediction model and the prediction weaning model for complete weaning having the most accurate validation result amongst the multiple prediction weaning models for complete weaning is selected to be the second designated weaning prediction model.

8. The method of claim 1, wherein when selecting at least one of the prediction weaning models for try-weaning to be the first designated weaning prediction model and when selecting at least one of the prediction weaning models for complete weaning to be the second designated weaning prediction model, the first designated weaning prediction model is selected based on an average value of the probabilities of success of weaning at the predetermined spans of time predicted by the multiple prediction weaning models for try-weaning, and the second designated weaning prediction model is selected based on an average value of the probabilities of success of weaning at the predetermined spans of time predicted by the multiple prediction weaning models for complete weaning.

* * * * *